US012797623B2

(12) United States Patent
Kohler et al.

(10) Patent No.: US 12,797,623 B2
(45) Date of Patent: Nov. 17, 2026

(54) MECHANICAL IMPACT PROTECTION FOR IMPLANTABLE HERMETIC ASSEMBLIES

(71) Applicant: CorTec GmbH, Freiburg (DE)

(72) Inventors: Fabian Kohler, Freiburg (DE); Juan Felipe Quiceno Quintero, Freiburg (DE); Maria Joao Guedes De Sousa, Freiburg (DE); Martin Schuettler, Emmendingen (DE)

(73) Assignee: CorTec GmbH, Freiburg (DE)

( * ) Notice: Subject to any disclaimer, the term of this patent is extended or adjusted under 35 U.S.C. 154(b) by 170 days.

(21) Appl. No.: 18/802,638

(22) Filed: Aug. 13, 2024

(65) Prior Publication Data

US 2024/0399158 A1 Dec. 5, 2024

Related U.S. Application Data

(63) Continuation of application No. PCT/EP2023/053629, filed on Feb. 14, 2023.

(30) Foreign Application Priority Data

Feb. 14, 2022 (DE) ..................... 10 2022 103 439.9

(51) Int. Cl.
*A61N 1/375* (2006.01)
*H05K 5/06* (2006.01)

(52) U.S. Cl.
CPC ......... *A61N 1/3758* (2013.01); *A61N 1/3754* (2013.01); *H05K 5/06* (2013.01)

(58) Field of Classification Search
CPC ................ A61N 1/3758; A61N 1/3754; A61N 1/36038; A61N 1/37512; A61N 1/37514; A61N 1/375; H05K 5/06
See application file for complete search history.

(56) References Cited

U.S. PATENT DOCUMENTS

| | | | | |
|---|---|---|---|---|
| 5,833,714 A * | 11/1998 | Loeb | ................. | A61N 1/36038 607/137 |
| 2003/0109903 A1* | 6/2003 | Berrang | ................. | A61N 1/375 607/36 |
| 2006/0200200 A1 | 9/2006 | Malinowski et al. | | |

(Continued)

FOREIGN PATENT DOCUMENTS

| | | | | |
|---|---|---|---|---|
| AU | 2019457443 A1 | 1/2022 | | |
| DE | 202019100590 U1 | 5/2020 | | |
| WO | WO-2021008688 A1 * | 1/2021 | ........... | A61N 5/0601 |

OTHER PUBLICATIONS

International Search Report with written opinion issued by the European Patent Office for International Patent Application No. PCT/EP2023/053629, mailed on May 15, 2023.

(Continued)

*Primary Examiner* — Paula J Stice
(74) *Attorney, Agent, or Firm* — Myers Wolin, LLC

(57) ABSTRACT

An implantable assembly is provided having a base portion, and a lid portion covering the base portion. The lid portion and the base portion define an interior hermetically sealed volume. The assembly has a protective structure which encloses the lid portion, the protective structure being adapted for protecting the interior volume against mechanical impacts. The assembly further includes a polymer layer which encapsulates the base portion, the lid portion, and the protective layer.

15 Claims, 8 Drawing Sheets

(56) References Cited

U.S. PATENT DOCUMENTS

| | | | | |
|---|---|---|---|---|
| 2012/0303105 | A1* | 11/2012 | Askarinya .......... | A61N 1/37512 29/874 |
| 2015/0087892 | A1 | 3/2015 | Tourrel et al. | |
| 2015/0314129 | A1* | 11/2015 | Perraud .............. | A61N 1/37512 607/116 |
| 2018/0303602 | A1 | 10/2018 | Leigh | |

OTHER PUBLICATIONS

Examination Notice issued for German Patent Application No. 10 2022 103 439.9 dated Dec. 12, 2022 with an English translation.

* cited by examiner

MECHANICAL IMPACT PROTECTION FOR IMPLANTABLE HERMETIC ASSEMBLIES

CROSS REFERENCE TO RELATED APPLICATIONS

This application is a continuation of International Application No. PCT/EP2023/053629, filed Feb. 14, 2023, which takes priority from German Patent Application No. 10 2022 103 439.9, filed on Feb. 14, 2022, the entire contents of each of which are incorporated by reference herein.

FIELD OF THE INVENTION

The invention relates to a mechanical protection for ceramic-based, implantable hermetic assemblies to increase their overall impact robustness. It relates in particular to assemblies for active implants intended to be implanted in the skull, where direct and hence higher impact energies are expected.

BACKGROUND

Implantable electronics must be protected from their liquid surrounding (body fluids) by a true hermetic barrier. True hermetic implies that the barrier material is impermeable to water and water vapor as well. This requirement is fulfilled by metals (such as titanium), glass or ceramic (e.g. alumina or zirconia). Along with the hermetic sealing requirement, electrical signals must be routed in and outside the hermetic package in order to satisfy the assembly's purpose. This is realized by electrical feedthroughs. Electrodes which serve as interface to the tissue are connected to these feedthroughs. The entire implant assembly of hermetic package, feedthrough and associated interconnected parts must be robust enough to withstand foreseeable mechanical impact loads when implanted in its intended location. Implant assemblies which are implanted in the skull are especially exposed to higher impact loads due to falls, external impacts or other. For this reason, such implants must fulfil normative requirements which are considerably higher when it comes to impact robustness, compared to other implants located in areas of the body less prone to impact exposure (e.g. pacemakers implanted in the patient's chest). State of the art standards for Cochlear implants (e.g. ISO 14708-7 or EN 45502-2-3) demand impact robustness of 2.5 Joules for a striking element directly hitting the implants most sensitive part. Here, impact robustness also includes full device functionality after impact.

While metals offer sufficient impact strength to build mechanically robust implantable packages, they lack the possibility to allow radio-frequency (RF) signals, alternating magnetic fields (inductive power supply) and (infrared) light to pass through the package wall. Additionally, due to a metal's conductive nature, the embodiment of a high number of electrical feedthroughs including individual feedthrough insulation, results in larger overall package volumes. Ceramic and glass packages in turn are inherently more brittle than metal and hence less robust when exposed to impact loads. However, they are sufficiently transparent to signals described above and can be used for high-channel hermetic packages. Packages require to be overmolded with a polymer such as polydimethylsiloxane (e.g. PDMS, epoxy or polyurethane) in order to ensure electrical insulation of the feedthroughs outside the package after lead or connector assembly. However, depending on the nature of the overmold (especially when elastomeric materials are used) the overmold is not suitable to sufficiently buffer impacts as considered to happen in typical applications. To utilize the advantages of non-metal packages, the following disclosure offers possibilities to increase their impact strength.

SUMMARY

It is an objective to provide a hermetic sealed assembly which alleviates at least one of the technical problems mentioned above.

Accordingly provided is an implantable assembly, comprising:

- a base portion, and a lid portion covering the base portion the lid portion and the base portion defining an interior hermetically sealed volume,
- a protective structure which encloses the lid portion,
- the protective structure being adapted for protecting the interior volume against mechanical impacts,
- further comprising a polymer layer which encapsulates the base portion, the lid portion and the protective structure.

Advantageously, the protective structure may further enclose the base portion.

Yet further, the protective structure may comprise a material which is at least one of polymer, metal, carbon, ceramic, and composite material.

Further, at least one section of the protective structure may be adapted to serve as electrically active contact area.

The interior hermetically sealed volume may enclose electronics. The protective structure may further enclose electric components in particular at least one of feedthroughs, pins, headers, wires, coils, antennas, electrical components, cables, electrodes.

The polymer layer may be made from at least one of PDMS, epoxy, and polyurethane.

The protective structure comprises a number of openings, in particular holes, slits, for fixation by the polymer layer.

The assembly may further comprise a number of metal contacts embedded in the protective structure.

The metal contacts may comprise metal platelets, in particular at least one of platinum, platinum-iridium, titanium, MP35N, stainless steel, or Nitinol, inserted in the protective structure.

Further, the metal contacts may be embedded with one of PDMS epoxy, and polyurethane.

The assembly may further comprise an element adapted as a strain relief for cables and/or connectors joined to the feedthroughs the element being integrally formed with the protective structure.

The contacts can be electrically connected to the feedthroughs beneath the protective structure.

The base portion and/or the lid portion may comprise at least one reinforced section serving as absorption or as contact points for the protective structure in particular chamfered edges, rounded edges, thicker walls.

Further provided may be attachment means for the protective structure, in particular at least one of notches, anchors, and snap fits.

Further, the protective structure may define at least one void-free space with the lid portion and/or with the base portion the at least one void-free space comprising at least one polymer.

Further, a space may be formed in the protective structure on top of the lid and a number of polymer layers are arranged therein, each of the layers having a respective Young's Modulus different from each other.

The protective structure may further comprise a number of different polymer layers with respective Young's modulus different from each other.

The protective structure may cover additionally to the lid portion and the base portion but also a coil and parts of a cable, which are located outside the internal volume, and may additionally form a guiding structure for the cable to the outside to form a strain relief for the cable.

The protective structure may sit on side walls of the lid portion.

The protective structure may be completely encapsulated by a polymer layer.

The polymer layer may also encapsulate the lid portion, the base portion, the feedthrough, and the coil, thus providing for biocompatibility of the assembly.

Thus, an assembly is provided made of ceramic (or sapphire, glass-ceramic or glass or another non-metallic material) which is reinforced by an additional surrounding structure to significantly improve its impact strength. This additional structure can be a mechanical frame or scaffold of different designs which allows to absorb mechanical impact and distribute the loads from impact sensitive parts, such as the package's center in whole or part to less sensitive areas such as the sides. Another realization of impact improvement is provided by encapsulation of the package with different material layers with varying Young's moduli. Such layers could be polymers such as elastomers or thermoplastic materials.

The impact protection not only shields sensitive parts of the hermetic package, but also components such as feedthroughs, wires, pins, coils and cables or at least transitions to the same.

Thus, embodiments of the invention provides an implantable assembly with a protective structure which surrounds the lid portion and the base portion (the hermetic package) and other impact sensitive parts of the active implantable assembly in part or in total.

The protective structure is designed and shaped to direct it from mechanically sensitive parts to more robust parts (e.g. from the center to the side walls), or to absorb kinetic energy leading to permanent or temporary deformation or to avoid demolition of the hermetic package and other parts (e.g. coils, antennas).

Since the hermetically sealed volume is in the core of the assembly it is best protected against deformation and thus against leakage. The parts which seal the interior volume are not for protecting against mechanical impact. That is, they will not deform and thus their hermetic sealing capability will not be reduced or destroyed. Only the protective structure is exposed to mechanical impacts but impacts and even a deformation thereof will not affect the sealing of the volume defined by the hermetic package.

BRIEF DESCRIPTION OF THE DRAWING

The invention and embodiments thereof will be described in more detail with reference to the drawings, wherein:

In FIG. 4B a metal contact is embedded in the protective structure;

In FIG. 7B a metal contact is embedded in the protective structure and not covered by polymer for direct exposure to the tissue;

DETAILED DESCRIPTION

Figure 1:
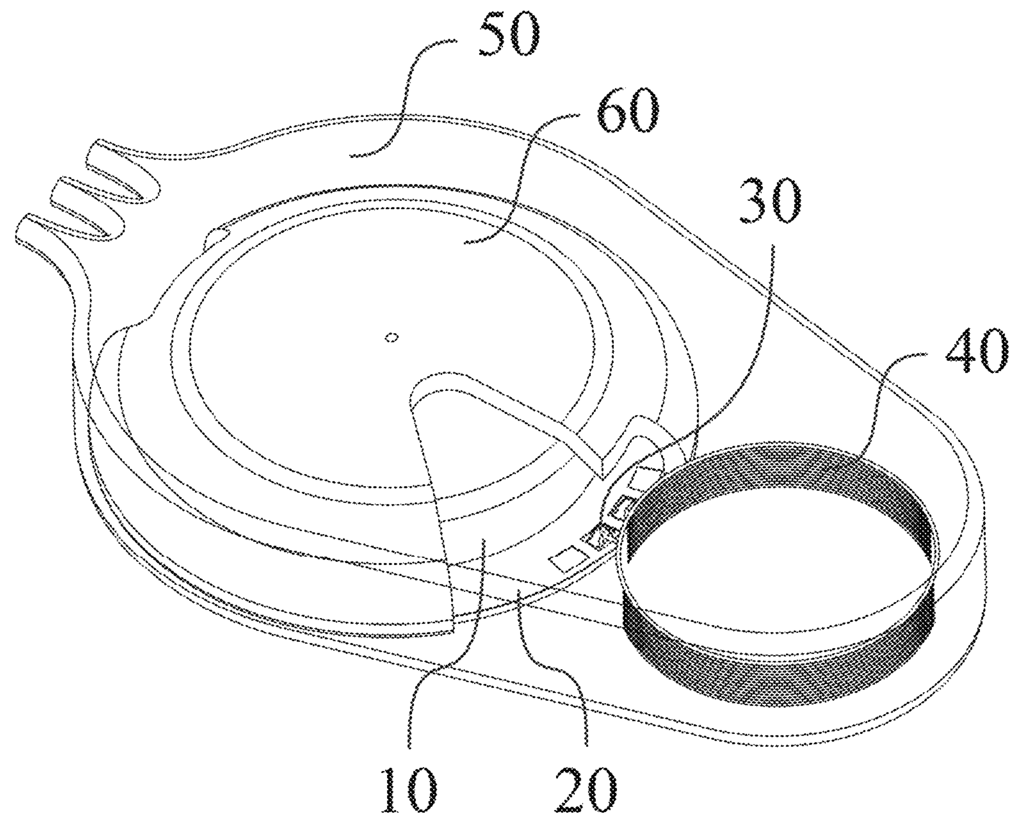
FIG. 1 illustrates an exemplary active implant with a protective cover on parts of the hermetic package; the protective structure is illustrated as sectional view to see underneath.
Figure 2:
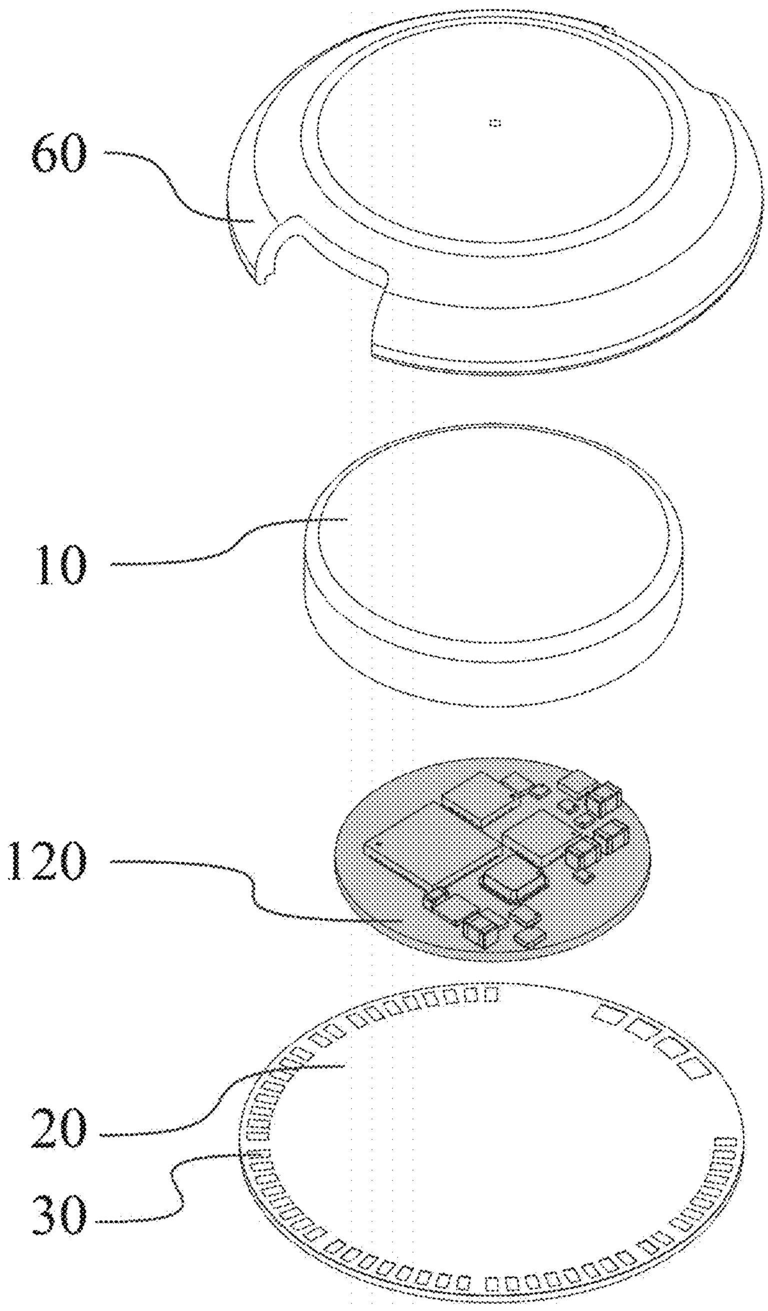
FIG. 2 illustrates a 3D exploded view of the hermetic package and protective structure.
Figure 3:
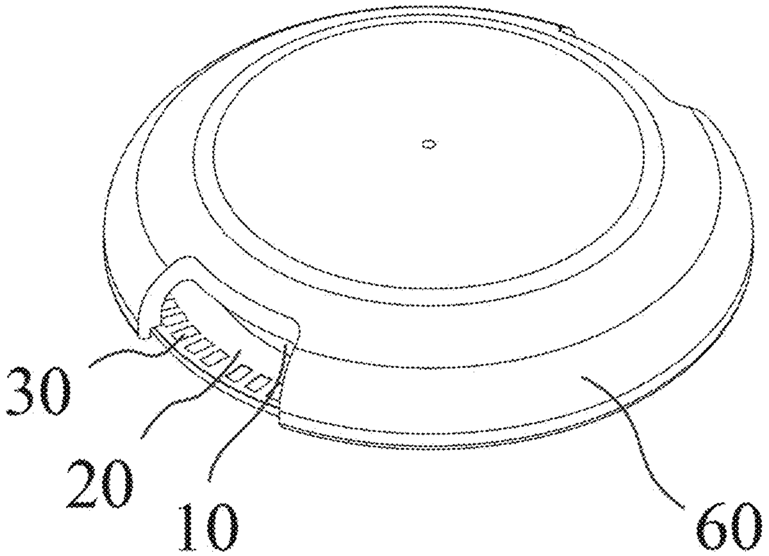
FIG. 3 illustrates the assembly of a hermetic package and a protective structure.

Referring to FIG. 1, an active implantable medical assembly is illustrated, comprising a hermetic package with a lid portion 10 and base portion 20, feedthroughs 30, interconnected components, e.g. a coil 40, and a polymer encapsulation, e.g. made of PDMS 50. The hermetic package 10, 20 is covered by a protective structure 60, on top of the lid portion 10 and parts of the base portion 20.

The lid portion 10 and base portion 20 define a hermetically sealed internal volume 15 in which electronics 120 is housed. Lid portion 10 and base portion 20 together are also denoted here as the hermetic package.

The protective structure 60 encloses the lid portion 20 and is adapted for protecting the interior volume 15 against mechanical impacts. Since the protective structure 60 is in contact only with the vertical edge of the lid portion 10 and with the base portion 20 it can deflect impacts on its top side onto the side walls of the lid portion, thus protecting the horizontal top area of lid portion 20 from the impacts.

Not illustrated in FIG. 1 but also part of embodiments of the invention is a protective structure 60 which also covers the backside of the implant building a share, oval or other enclosing shape.

Figure 11:
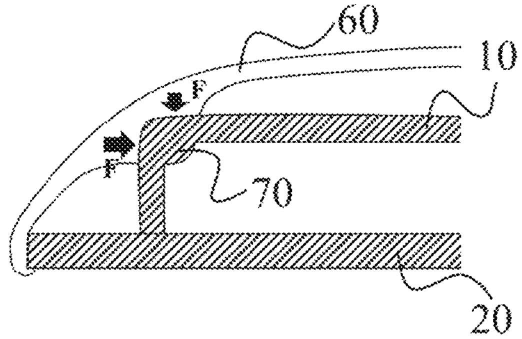
FIG. 11 illustrates the modification of the hermetic package's lid on the inside to counteract forces from the protective structure after impact.

FIG. 2-FIG. 5 show different views of the assembly. Exploded and sectional views enable visibility in the enclosed electronics 120 inside the hermetic package 10, 20. Inside the hermetic package 10, 20 the lid portion's 10 side walls are directly opposing the protective structure and in case of impact, the energy shall be distributed to the same. To additionally reinforce the walls, internal structures 70, such as radii, chamfers, or similar can be added to the lid's inside as depicted in FIG. 11.

Figure 4A:
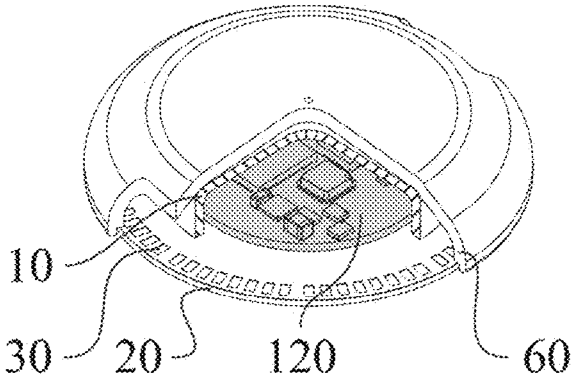
FIGS. 4A-B illustrate the assembly of a hermetic package and a protective structure in a view where parts of the package are cut to view inside.
Figure 4B:
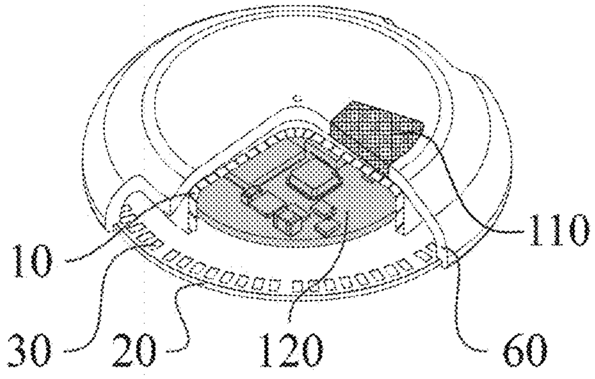
Figure 5:
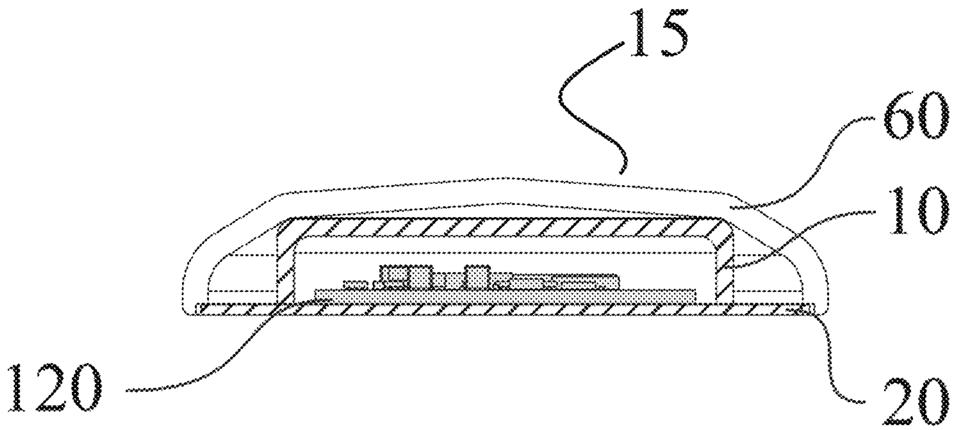
FIG. 5 illustrates the assembly of a hermetic package and a protective structure in a sectional view.
Figure 6A:
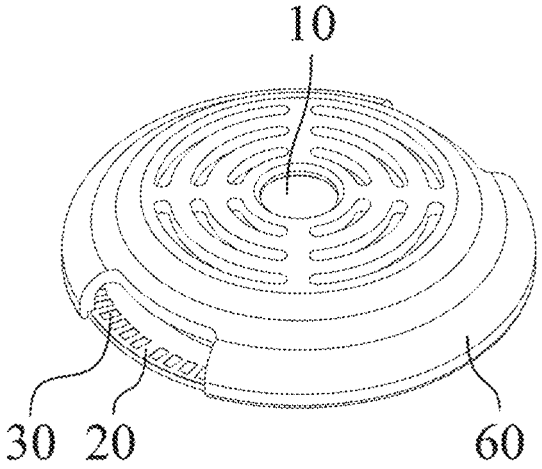
FIGS. 6A-D illustrate four exemplary designs of the protective structure.
Figure 6B:
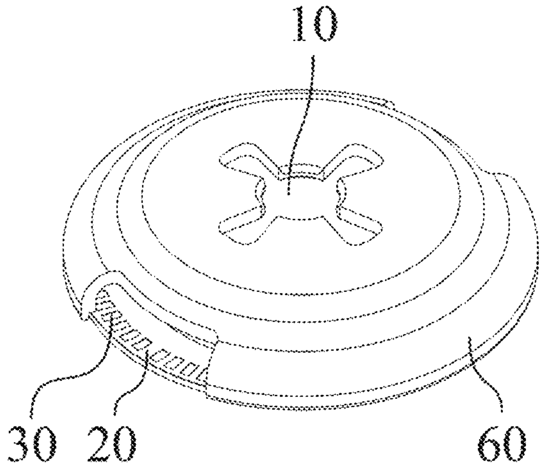
Figure 6C:
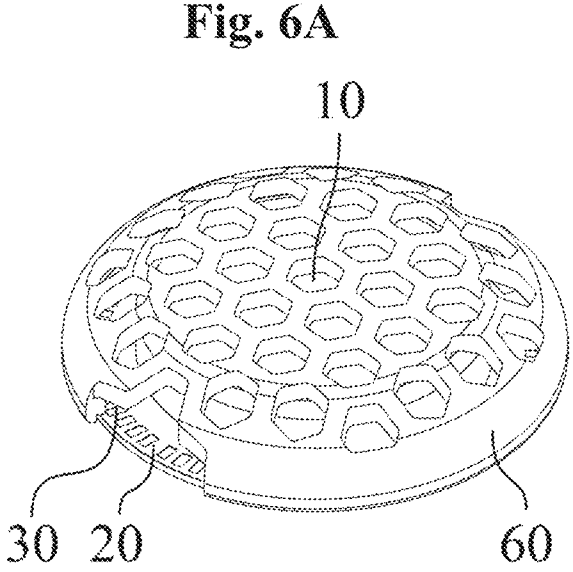
Figure 6D:
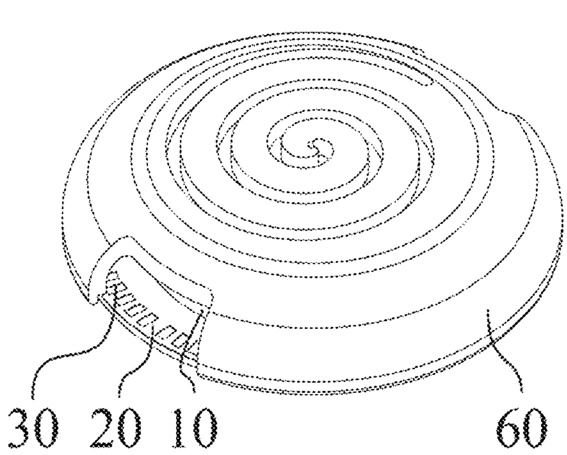

FIG. 4B shows the additional embedding of a metal contact 110 in the protective structure 60. The contact can be electrically connected to a feedthrough 30 beneath the protective structure 60. Spacings within the protective structure 60 might be added as needed. Another option to embed a metallic contact is the realization of the protective structure 60 out of a conductive material, such as metal and leave parts of the structure exposed to the tissue when embedded in polymer.

The metal contact 110 can be for electrical stimulation, sensing neural signals or for other purposes.

In FIGS. 6A-D, the protective structure 60 is shaped according to different designs, such as rings, spirals, honeycombs or openings of various shapes, crosshatches, parallel lines, meshes, random lines, solid planes with or without holes, poles, stacked layers. Theses designs can be adapted to the needs of application, shape of the assembly or to allow better mechanical anchoring within the surrounding polymer encapsulation 50, 100 described below. The depicted designs are only examples and depending on the individual implant design, partial covering of the protective structure 60 might be desired.

Figure 7A:
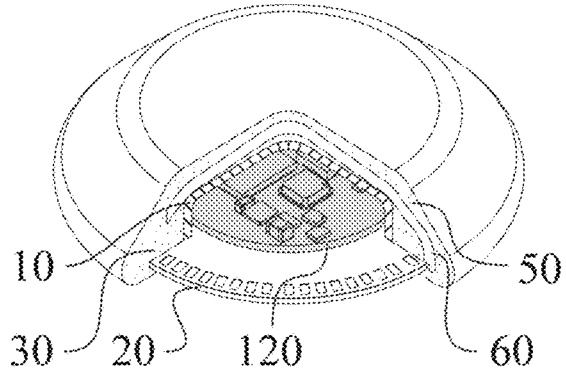
FIGS. 7A-B illustrate the assemblies of FIGS. 4A-B but additionally overmolded with a Polymer.
Figure 7B:
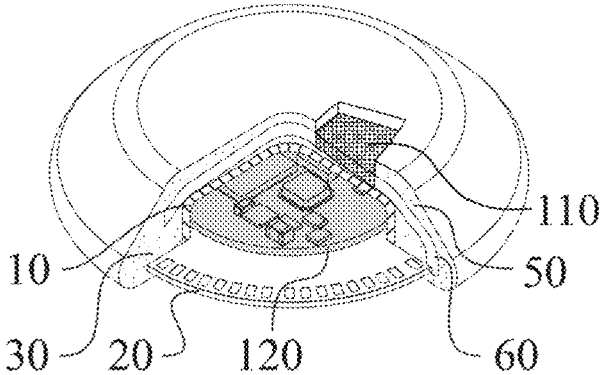
Figure 8:
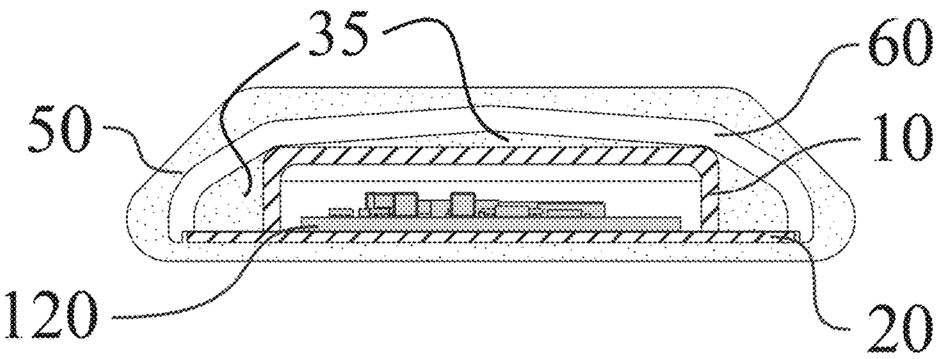
FIG. 8 illustrates the assembly of FIGS. 7A-B in a sectional view.

To firmly secure the protective structure 60 and to ensure the implant assembly's biocompatibility for all materials in direct contact to the tissue, the protective structure is encapsulated in polymer 50, such as PDMS. FIGS. 7A-B and FIG. 8 illustrate the presence of the polymer encapsulation 50. The protective structure 60 can be designed with particular gaps to facilitate void-free filling of spaces 35 beneath the protective structure 60 with polymer. If a metal contact 110 is embedded in the protective structure 60, the polymer encapsulation 50 shall not cover the metal contact 110 to expose it to the tissue.

Electrical connections can be realized by attaching a wire to the metal contact 110 (e.g. backside) and routing it beneath the protective structure 60.

Figure 9:
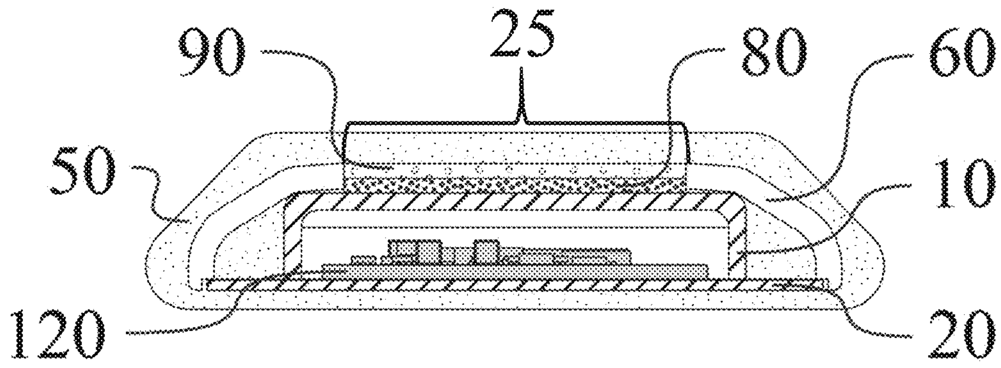
FIG. 9 illustrates the assembly of FIGS. 7A-B in a sectional view, but the protective structure serves as side wall for a multi-layer of polymers with varying Young's Moduli.

In FIG. 9, the protective structure 60 forms a space 25 on top of the lid portion 10, which is completely filled up with layers 80, 90 of different polymers. In FIG. 9 two polymers layers 80, 90, one layer 90 with Young's Modulus A and a second layer 80 with Young's Modulus B are illustrated. However, the layer stack is not limited to two layers 80, 90 but whatever is suitable for application and design of the hermetic assembly and protective structure 60 which forms the side walls. The polymer layers 80, 90 act as impact protection by absorbing the impact rather than deflecting it.

The polymer layers with respective different Young's modulus are to achieve a gradient soft-to-hard or vice versa across the layers. Preferably more than two such layers are provided. Typical polymer materials for these layers are PDMS, epoxies, polyurethanes. The polymers might be applied in liquid state or applied as foam or be mixed with fillers or particles to modify their Young's modulus. To achieve lateral gradients, different materials or amounts of fillers can be utilized in segments of one layer which are next to each other.

The assembly may further comprise additional layers of polymer mesh, sheets or foil. Polymer meshes, sheets and foils can be made of polyester (PE), polyetheretherketone (PEEK), polypropylene (PP), parylene or any other suitable polymer.

Yet further, the assembly may comprise marker elements for identification of the assembly, and/or of the protective structure 60. The protective structure 60; 80, 90 may further comprise a transparent polymer which allows optically reading the marker elements.

Another possibility for device identification is the placement of an identification tag between protective structure and surrounding PDMS encapsulation or between layers of different polymers.

Figure 10:
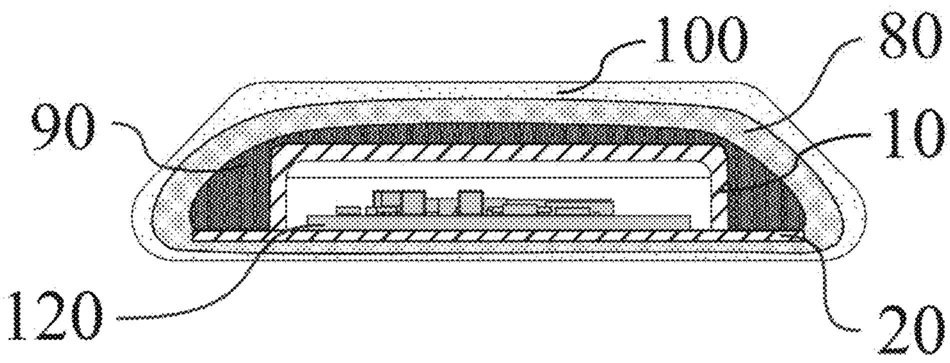
FIG. 10 illustrates a protective structure entirely made of polymer layers with different young's modulus.

FIG. 10 shows a hermetic package 10, 20 which is surrounded by a protective structure 80, 90 entirely made from different layers of polymers. Again, in this example two layers of varying Young's Modulus 80, 90 and a surrounding encapsulation of Young's Modulus C 100 are depicted. More layers are also conceivable. Again, the polymer layers 80, 90 act as impact protection by absorbing the impact rather than deflecting it.

Depending on the configuration and implant design, the protective structure 60 might extend to the base portion 20 or only cover the lid portion 10 and some adjacent structures such as cables, wires, coil 40, feedthroughs 30 etc.

Figure 12:
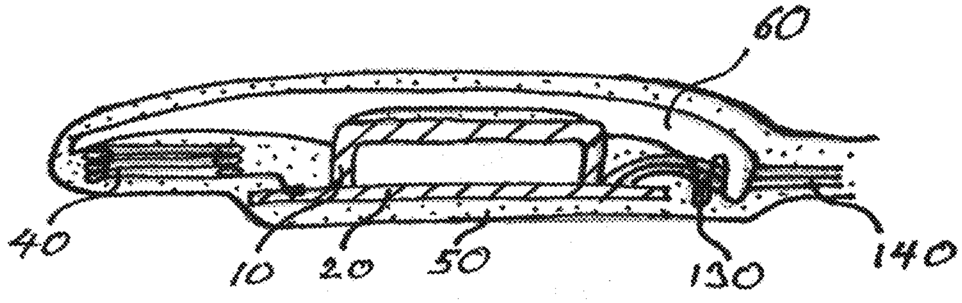
FIG. 12 illustrates the assembly of FIGS. 7A-B in a sectional view with the protective structure covering additional parts of the implant (coil and wires) and also forming a strain relief.

FIG. 12 shows an assembly with a protective structure 60 covering not only the lid portion 10 and the base portion 20 but also the coil 40 and parts of the cable 140, which are outside the internal volume 15 and additionally introduces a guiding structure for the cable or wire to the outside to form a strain relief 130. The protective structure 60 sits on the side walls of the lid portion 10. It is completely encapsulated by a polymer layer 50. The polymer layer 50 also encapsulates the lid portion 10, the base portion 20, the feedthrough 30, and the coil 40, thus providing for biocompatibility of the assembly.

The protective structure 60 can be manufactured by means of additive or subtractive fabrication.

The protective structure 60 can be assembled from multiple parts to extend its coverage and thus protection to particular directions of the package. Multiple parts might also be assembled in a way to protect the package from all sides and create an all-enclosing structure.

LIST OF REFERENCE NUMERALS

10 Lid/lid portion of hermetic package/volume
15 Hermetically sealed volume
20 Base/base portion of hermetic package/volume
25 Space in the protective layer on top of the lid 10
30 Electrical feedthrough
35 Void-free space
40 Coil
50 (Polymer) encapsulation
60 Protective structure
70 Modified internal structure of the hermetic package (e.g. lid)
80 Polymer layer with Young's Modulus A
90 Polymer layer with Young's Modulus B
100 Surrounding polymer layer with Young's Modulus C
110 Electrical contact area (exposed), metal contact
120 Electronics
130 Strain relief for cable
140 Cable to electrodes or connectors

What is claimed is:

1. An implantable assembly, comprising:
a base portion, and a lid portion covering the base portion, the lid portion and the base portion defining an interior hermetically sealed volume,
a protective structure which encloses the lid portion,
the protective structure being adapted for protecting the interior volume against mechanical impacts,
further comprising a polymer layer which encapsulates the base portion, the lid portion, and the protective structure (60; 80, 90); and
wherein a space is formed in the protective structure on top of the lid portion and a number of polymer layers are arranged therein, each of the layers having a respective Young's Modulus different from each other.

2. The assembly of claim 1, wherein the protective structure further encloses the base portion.

3. The assembly of claim 1, wherein the protective structure comprises a material which is at least one of polymer, metal, carbon, ceramic, and composite material.

4. The assembly of claim 1, wherein at least one section of the protective structure is adapted to serve as electrically active contact area.

5. The assembly of claim 1, wherein the interior hermetically sealed volume encloses electronics.

6. The assembly of claim 1, wherein the protective structure further encloses electric components.

7. The assembly of claim 1, wherein the polymer layer is made from at least one of PDMS, epoxy, and polyurethane.

8. The assembly of claim 1, wherein the protective structure comprises a number of openings for fixation by the polymer layer.

9. The assembly of claim 1 further comprising a number of metal contacts embedded in the protective structure.

10. The assembly of claim 9, wherein the metal contacts comprise metal platelets.

11. The assembly of claim 10, wherein the metal contacts are embedded with one of PDMS epoxy, and polyurethane.

12. The assembly of claim 1 further comprising an element adapted as a strain relief for cables and/or connectors joined to the feedthroughs, the element being integrally formed with the protective structure.

13. The assembly of claim 1, wherein the base portion and/or the lid portion comprise at least one reinforced section serving as absorption or as contact points for the protective structure.

14. The assembly of claim 1, wherein the protective structure defines at least one void-free space with the lid portion and/or with the base portion, the at least one void-free space comprising at least one polymer.

15. The assembly of claim 1, wherein the protective structure comprises a number of different polymer layers with respective Young's modulus different from each other.

* * * * *